(12) United States Patent
Ownby et al.

(10) Patent No.: US 10,317,324 B1
(45) Date of Patent: Jun. 11, 2019

(54) SPECIMEN TESTING SYSTEMS AND METHODS

(71) Applicant: Board of Trustees of the University of Alabama, fo, Huntsville, AL (US)

(72) Inventors: Kalob Ownby, Florence, AL (US); Mark Creel, Cullman, AL (US); Jordan Fulmer, Huntsville, AL (US); Matt Fulmer, Muscle Shoals, AL (US); Michael Henry, Madison, AL (US); Dung Tuan Le, Opelika, AL (US); Melissa Lee, Madison, AL (US); Derek Odom, Ardmore, AL (US); Russ Walton, Hunsville, AL (US); Jeffrey Evans, Priceville, AL (US)

(73) Assignee: Board of Trustees of the University of Alabama, for and on behalf of the University of Alabama in Huntsville, Huntsville, AL (US)

(*) Notice: Subject to any disclaimer, the term of this patent is extended or adjusted under 35 U.S.C. 154(b) by 0 days.

(21) Appl. No.: 15/900,063

(22) Filed: Feb. 20, 2018

Related U.S. Application Data

(63) Continuation of application No. 14/745,339, filed on Jun. 19, 2015, now abandoned.

(60) Provisional application No. 62/014,357, filed on Jun. 19, 2014.

(51) Int. Cl.
| *G01N 3/20* | (2006.01) |
| *G01N 3/22* | (2006.01) |
| *G01N 3/26* | (2006.01) |
| *G01N 3/08* | (2006.01) |
| *G01N 3/04* | (2006.01) |

(52) U.S. Cl.
CPC .............. *G01N 3/20* (2013.01); *G01N 3/04* (2013.01); *G01N 3/08* (2013.01); *G01N 3/22* (2013.01); *G01N 3/26* (2013.01); *G01N 2203/0023* (2013.01); *G01N 2203/0037* (2013.01)

(58) Field of Classification Search
CPC .. G01N 3/04; G01N 3/08; G01N 3/20; G01N 3/22; G01N 3/26; G01N 2203/0021; G01N 2203/0023; G01N 2203/0026; G01N 2203/0028; G01N 2203/0037
USPC .......... 73/788, 847, 848, 849, 852, 853, 856
See application file for complete search history.

(56) References Cited

U.S. PATENT DOCUMENTS

| 2,787,157 A | 4/1957 | Angevine |
| 3,620,071 A | 11/1971 | Kelly |
| (Continued) | | |

OTHER PUBLICATIONS

Ownby, et al., U.S. Appl. No. 14/745,339, entitled, "Specimen Testing Systems and Methods," filed Jun. 19, 2015.

*Primary Examiner* — Benjamin R Schmitt
(74) *Attorney, Agent, or Firm* — Maynard Cooper & Gale, P.C.; Jon E. Holland

(57) ABSTRACT

A specimen testing system has holders that hold a specimen for testing. The holders brace the specimen so that a load may be applied. A load applicator applies a load to the specimen at a location that is between the holders bracing the specimen. A user may adjust the load applicator until it applies the desired load to the specimen. If desired, a user may apply rotation to a specimen while it is experiencing a load by using a specimen rotation system. The user may continue to adjust the load applied to the specimen or continue to rotate the specimen during loading until the specimen fails.

18 Claims, 3 Drawing Sheets

(56) References Cited

U.S. PATENT DOCUMENTS

| | | | | |
|---|---|---|---|---|
| 5,178,017 A | * | 1/1993 | Dinzburg | ........... G01N 3/20 73/849 |
| 6,663,617 B1 | | 12/2003 | Vito | |
| 2004/0016301 A1 | | 1/2004 | Moreno | |
| 2006/0213281 A1 | | 9/2006 | Doak | |
| 2014/0260579 A1 | | 9/2014 | Rashidi et al. | |

* cited by examiner

SPECIMEN TESTING SYSTEMS AND METHODS

CROSS REFERENCE TO RELATED APPLICATION

This application is a continuation of and claims priority to U.S. patent application Ser. No. 14/745,339, entitled "Specimen Testing Systems and Methods" and filed on Jun. 19, 2015, which is incorporated herein by reference. U.S. patent application Ser. No. 14/745,339 claims priority to U.S. Provisional Patent Application No. 62/014,357, entitled "Rotational Bending Fatigue and 3-Point Bending Machine" and filed on Jun. 19, 2014, which is incorporated herein by reference.

STATEMENT REGARDING FEDERALLY SPONSORED RESEARCH OR DEVELOPMENT

This invention was made with Government support under DMR-1151109 awarded by the National Science Foundation. The Government has certain rights in the invention.

RELATED ART

Conventional systems for testing a linear specimen cause bending in the specimen by applying weights to locations adjacent the ends of the specimen. Characteristics of the specimen may then be determined, such as the strength of the specimen. However, such testing requires of a wide variety of varying weights in order to ensure that the desired load is applied as accurately and precisely as possible. Nevertheless, even with a wide variety of weights available, precise adjustment of the load applied to the specimen remains difficult, especially when rapid load adjustment is necessary. It is also burdensome for the user to keep and store a multitude of weights for use during testing.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

The present disclosure generally pertains to a specimen testing system. In one exemplary embodiment, a user places a linear specimen (e.g., a plank, a shaft, a rod, or a tube) for which testing is desired into the loading system by inserting the specimen into a plurality of specimen holders. The specimen holders use adjacent holders separated by a distance to brace portions of the specimen. An adjustable load applicator is configured to apply a load to the specimen in a direction that is approximately perpendicular to the specimen's longitudinal axis and at a location on the specimen that is between the holders. The user adjusts the load applicator until the applicator applies a desired load to the specimen (i.e., until the specimen experiences a desired force from the applicator). The system allows the user to measure deflection of the specimen and the applied load. If desired, the user may continue to adjust the load applicator to increase the load applied to the specimen until the specimen fails. Alternatively, after applying the desired load, the user may use a specimen rotation system coupled to at least one of the holders to rotate the specimen about its longitudinal axis. The user may continue to rotate the specimen while the specimen is experiencing a load applied by the load applicator until the specimen experiences a desired load or fails (i.e., the specimen experiences fatigue that exceeds its maximum rotational bending fatigue).

Figure 1:
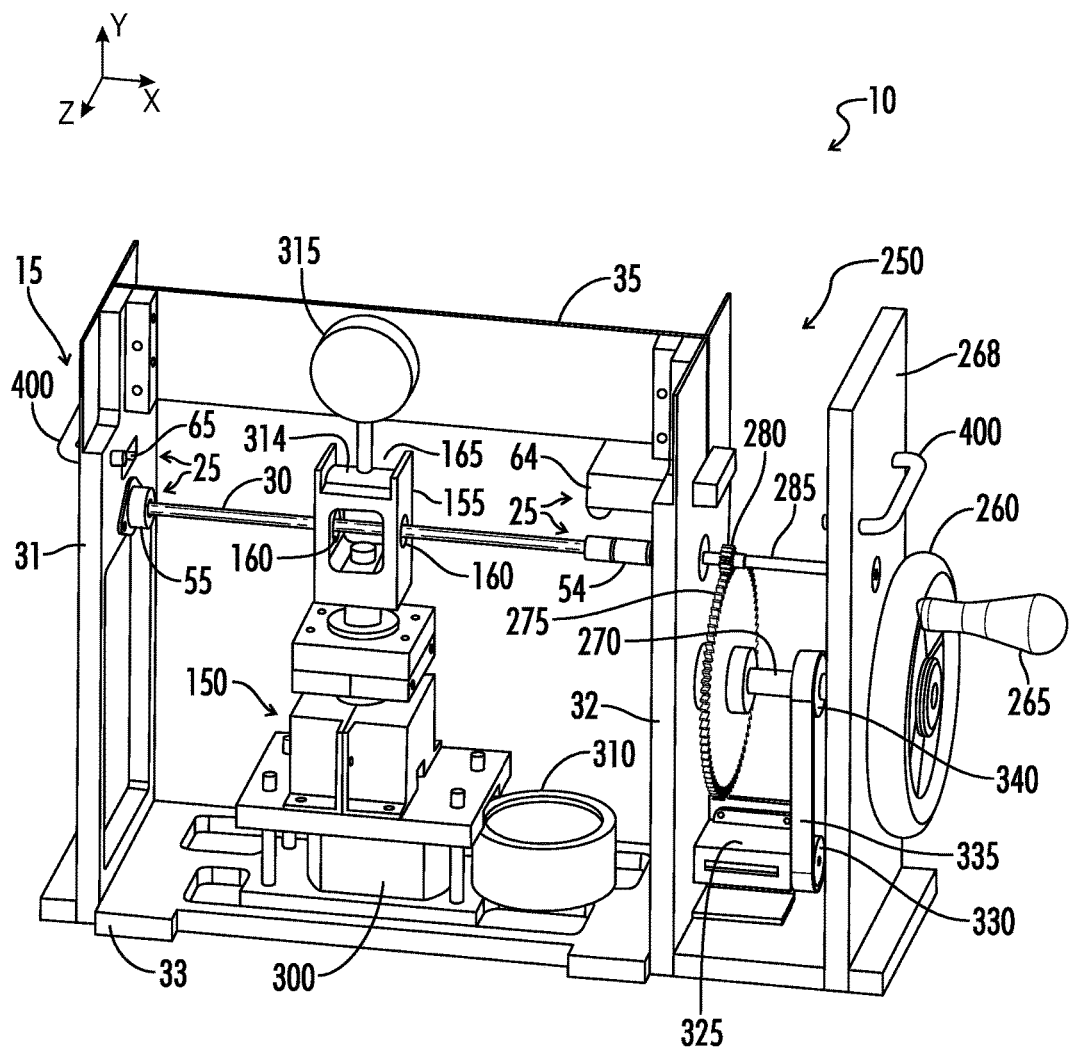
FIG. 1 is a three-dimensional perspective view illustrating an exemplary embodiment of a system for loading specimens configured for loading a specimen and rotating the specimen using a specimen rotation system.

FIG. 1 depicts an exemplary embodiment of a specimen testing system 10. The loading system 10 comprises a frame 15 having a plurality of specimen holders 25 for holding a specimen 30. Note that the system 10 depicted by FIG. 1 is configured for loading a specimen 30 and rotating the specimen 30 using techniques described below. The specimen holders 25 brace a specimen 30 placed in the testing system 10 so that a load may be applied to the specimen 30 at a location between the ends of the specimen 30, as described in further detail below. In the exemplary embodiment shown by FIG. 1, a specimen 30 is coupled to holders 25 of the frame 15. The frame 15 comprises a left support 31, a right support 32, a base member 33, and connecting beam member 35. The supports 31 and 32 are composed of a suitable material (e.g., aluminum), rectangular in shape, and roughly parallel in orientation with respect to one another. As shown in FIG. 1, a bottom end of each support 31 and 32 is mounted on the base member 33, and the top ends of the supports 31 and 32 are coupled to one another by the connecting beam member 35. In other embodiments, other configurations of the frame 15 capable of stably supporting the holders 25 may be used, and it is not necessary for the supports 31 and 32 to be parallel.

The base member 33 shown in the embodiment depicted by FIG. 1 is composed of a suitable material, rectangular in shape and generally flat and is coupled to the left support 31 and right support 32 at their respective bottom ends. Note that the base member 33 has sufficient surface area on a bottom surface of the base member 33 to allow the system 10 to remain stationary and stable during operation. In this regard, the base member 33 provides stability and support while the system 10 applies a load to a specimen 30 as described further below. Other suitable shapes and configurations for the base member 33 are possible in other embodiments. In embodiments without a base member 33, the system 10 may be supported in a sufficiently stable manner by other suitable means.

The beam member 35 shown in the embodiment depicted by FIG. 1 is composed of a suitable material (e.g., aluminum), rectangular in shape and generally flat. In the embodiment shown by FIG. 1, the beam member 35 is oriented such that its transverse axis is approximately perpendicular to the transverse axis of the base member 33, and is coupled to each of the left support 31 and right support 32 near their respective upper portions. In this regard, it provides sufficient stability against movement for the system 10 to operate. Note that, in the instant embodiment, the beam member 35 is positioned above but adjacent to a specimen 30 placed in and coupled to the holders 25 of the system 10, as described below. While the beam member 35 in one embodiment serves to enhance stability and provide support for the supports 31 and 32, in other embodiments, the beam member 35 further may comprise a device (e.g., a ruler or gauge) for measuring deflection of a specimen 30 after a load is applied to the specimen 30, as further described below.

The holders 25 of the system 10 can take any suitable combination of forms for securely holding a specimen 30 in a variety of embodiments. In the exemplary embodiment shown by FIG. 1, the specimen holders 25 holding the specimen 30 are implemented as a conventional chuck 54 and a bearing 55. FIG. 1 also shows holders 25 implemented as a stop 64 and a slot 65 that are not specifically depicted as holding a specimen 30. Other holders 25 are possible in other embodiments.

The holder 25 implemented as a chuck 54 depicted by FIG. 1 is coupled to the right support 32 of the system 10. The chuck 54 securely grips the specimen 30 according to known techniques (e.g., using jaws, dogs, sleeves, or collets) and is rotatable about the longitudinal axis of the specimen 30. Note that a user inserts one end of the specimen 30 into the chuck 54 and then tightens the chuck 54 until it fits securely around the specimen 30 by providing or increasing friction between the chuck 54 and the specimen 30. In this regard, the chuck 54 grips the specimen 30 with sufficient force to prevent the specimen 30 from moving independently of the chuck 54. In one embodiment, the chuck 54 may be tightened with sufficient force to grip the specimen 30 using only force supplied by a user's hand, but other techniques for tightening the grip of the chuck 54 on the specimen 30 are possible in other embodiments. In yet other embodiments, the holding system 25 may comprise other suitable devices capable of gripping the specimen 30 securely during rotation.

As shown by FIG. 1, the specimen 30 is inserted into a holder 25 implemented as a bearing 55 coupled to the left support 31 opposite the chuck 54. The bearing 55 stabilizes the specimen 30 and permits the specimen 30 to rotate about its longitudinal axis while coupled to the chuck 54. In one embodiment, the bearing 55 is implemented as a plain bearing, such as a journal bearing, for example, but other suitable bearings are possible in other embodiments (e.g., bushings, sleeve bearings, roller bearings, ball bearings, or fluid bearings). In this regard, the bearing 55 makes contact with a surface of the specimen 30 and permits the specimen 30 to experience rotation applied by the chuck 54 when implemented by a user while bracing the specimen 30 against movement. Additionally, in the instant embodiment, the specimen 30 passes completely through the bearing 55 and left support 31 via corresponding holes in the bearing 55 and support 31 that are aligned before coupling to the chuck 54 that is coupled to the right support 32. In other embodiments, the there is no hole in the left support 31 for the specimen 30 to pass through such that the left support 31 functions as a stop to prevent further movement of the specimen 30 as it is being inserted into the bearing 55.

Figure 2:
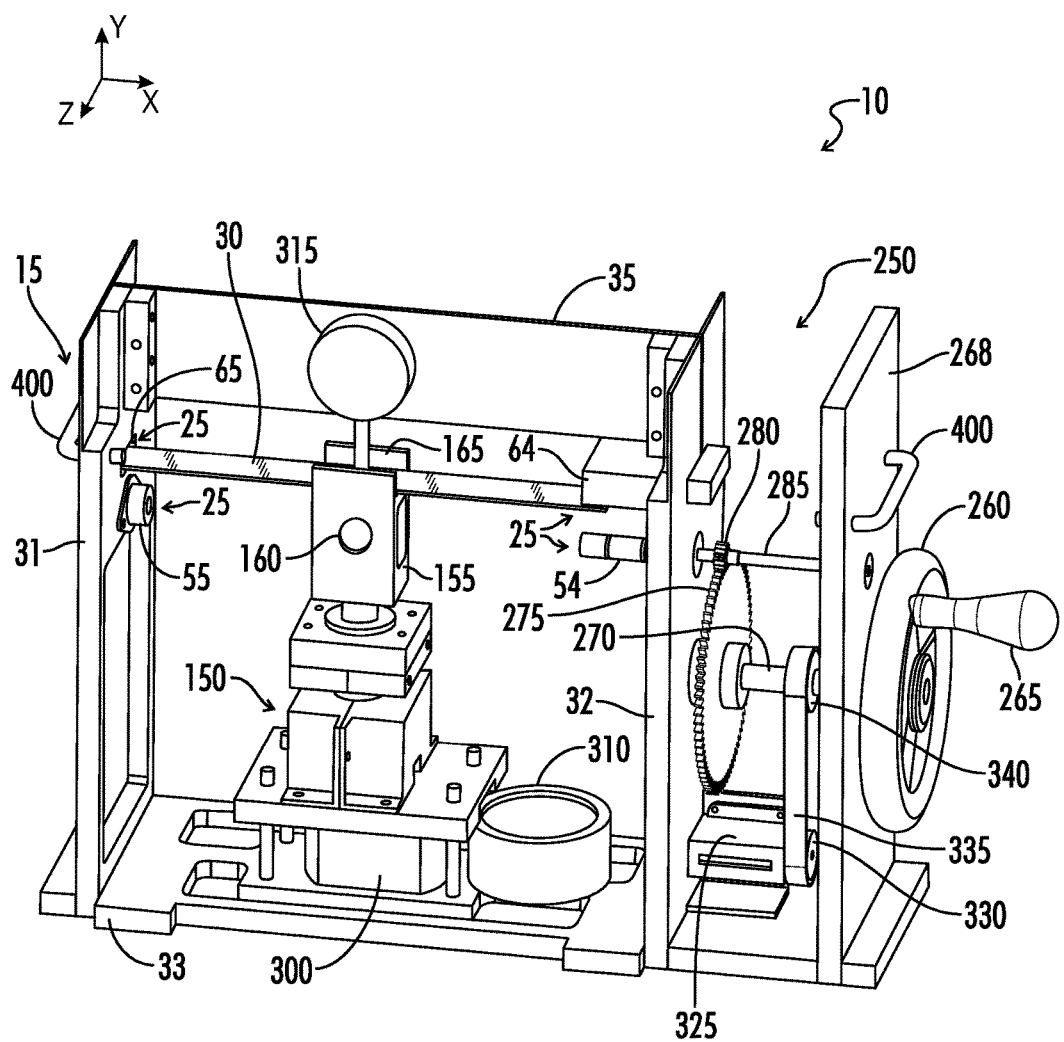
FIG. 2 is a three-dimensional perspective view illustrating an exemplary embodiment of a system for loading specimens configured for loading a specimen without rotating the specimen using a specimen rotation system.

FIG. 2 depicts an exemplary embodiment of the system 10 configured for loading a specimen 30, but not rotating the specimen 30, as may be performed by the system 10 depicted by FIG. 1. In the embodiment of FIG. 2, one of the holders 25 comprises stop 64 coupled to the right support 32 of the system 10. In an exemplary embodiment, a user inserts an end of a specimen 30 under the stop 64 when the user desires to apply a load to the specimen 30 (i.e., so that the specimen experiences bending), but not rotation. FIG. 2 depicts a flat specimen 30, but the stop 64 may hold a specimen 30 of any shape for testing in other embodiments. Note that the stop 64 may be any device suitable for holding the specimen 30 securely during bending in other embodiments (e.g., a clamp). When the stop 64 is implemented as a clamp, it is configured to adjust to apply sufficient pressure to grip an end of a specimen 30 that is inserted into the clamp 64 during bending of the specimen 30. Note that the clamp 64 may be adjustable by a user using only force applied by hand. In the instant embodiment, the stop 64 is configured to adjust to apply sufficient friction at points of contact between the stop 64 and a specimen 30 to brace the specimen 30 against movement. In this regard, the stop 64 adjusts to apply sufficient pressure to increase frictional forces and grip the specimen 30, but in other embodiments, the stop 64 may grip the specimen 30 by other suitable means. In one embodiment, a user may adjust the stop 64 to apply sufficient pressure a specimen 30 using the user's hand force only. The stop 64 may be adjustable by other means in other embodiments.

FIG. 2 further depicts a left support 31 comprising a holder 25 having as a slot 65 opposite the location of the stop 64. The slot 65 is oversized relative to a specimen 30 for which testing is desired, such that it can accommodate specimens 30 in a wide variety of sizes. A user inserts a specimen 30 into the slot 65, such that the specimen 30 passes completely through the left support 31 and may be inserted it into the stop 64 opposite the slot 65. When a load is applied to the specimen 30, a portion of the specimen 30 makes contact with an upper wall of the slot 65 as the specimen 30 undergoes deflection, preventing further movement in the Y-axis direction shown by FIG. 2. In this regard, the slot 65 stabilizes the specimen 30 and prevents movement with respect to the slot 65 when a user applies a load in the Y-axis direction to the specimen 30 at points where it makes contact with the slot 65, as described above (i.e., when a load is applied to the specimen 30 while inserted under the stop 64 such that the specimen 30 experiences deflection or bending). Note that in the exemplary embodiment depicted by FIG. 2, the slot 65 has a roughly rectangular shape and is sized to accommodate a specimen 30 having a corresponding cross section, but other shapes of the slot 65 are possible in other embodiments. In sum, the slot 65 and stop 64 brace the specimen 30 against movement in the direction of the load when a load is applied to the specimen 30 so that deflection of the specimen 30 may occur. In other embodiments, it is not necessary for the slot 65 to pass completely through the left support 31, or for the specimen 30 to pass completely through the slot 65.

In an exemplary embodiment, the system 10 applies a load to a specimen 30 via a load applicator 150. The load applicator 150 is adjustable such that a user can make precise adjustments to the load applicator 150 to apply the desired load to the specimen 30. The applicator 150 shown in FIG. 1 is implemented as a conventional mechanical jack, but other load applicators 150 are possible in other embodiments. Note that the height of the jack 150 may be adjusted upward or downward. In the instant embodiment, the jack 150 is mounted on the base member 33 and situated between the left support 31 and right support 32 below the specimen 30 such that, when actuated, the jack 150 extends in a direction that is roughly perpendicular to the longitudinal axis of the specimen 30 (i.e., the Y-axis direction). When the jack 150 reaches the height of the specimen 30, the jack 150 applies a load to the specimen 30 in the Y-axis direction at a location that is between points where the specimen 30 contacts its respective holders 25. Note that the load applied to the specimen 30 increases with each actuation of the jack 150 that increases the height of the jack 150. In this regard, the user can adjust the height of the jack 150 by actuating the jack 150, thereby increasing or decreasing the load applied to the specimen 30. The user may do so until the desired load is applied to the specimen 30.

Note that, while the jack 150 shown in FIG. 1 is coupled to the base member 33, it is not necessary for the jack 150 to be coupled to the base member 33 in other embodiments. In embodiments where the jack 150 is not coupled to a base member 33, the jack 150 is configured such that it can suitably apply a load to a specimen 30 coupled to the holders 25 via other means.

As shown by the exemplary embodiment of FIG. 1, the load applicator 150 has an interface 155 such that the interface 155 interacts with a specimen 30 to which the applicator 150 is applying a load. Note that the interface 155 is configured to interact with a specimen 30 such that the load applicator 150 applies the desired load to the specimen 30 suitably for testing purposes (i.e., the load is applied stably and consistently). In one embodiment, the interface 155 is configured to accommodate specimens 30 of a variety of shapes and sizes. For example, in the exemplary embodiment depicted by FIG. 1, the interface 155 is configured to accommodate specimens 30 having either a round cross section (e.g., a shaft, rod or tube) or specimens 30 having a rectangular cross section (e.g., a plank). The interface 155 may accommodate a variety of specimens having any cross-sectional shape in other embodiments.

The interface 155 shown by FIG. 1 has holes 160 aligned such that a specimen 30 can pass through both holes 160 of the interface 155 (i.e., the holes 160 receive the specimen 30). Note that it in some embodiments, the interface 155 only comprises one hole 160 for receiving the specimen 30. In other embodiments, the interface 155 comprises two or more holes 160 for receiving a specimen 30, where each of the holes 160 is separated by a hollow region. When the load applicator 150 applies a load in the Y-direction, inner walls of each hole 160 contact a portion of the specimen 30, such that the force from the load applicator 150 is applied to the specimen 30 at these points of contact. In this regard, the interface 155 directs the load applied by the load applicator 150 to the specimen 30. In other embodiments, the holes 160 may have different shapes to accommodate specimens 30 of various cross sections.

Additionally, in the embodiment shown by FIG. 2, the interface 155 has a face 165 that is oriented to make contact with a surface of the specimen 30 when the applicator 150 is applying a load in the Y-axis direction. As shown by FIG. 2, the face 165 is positioned on a top side of the interface 155. In an exemplary embodiment, when a user places a specimen 30 through the slot 65 (i.e., from the X-axis direction) and inserts it under the stop 64, the face 165 is parallel to a surface of the specimen 30.

Note that it is generally desirable for the face 165 to have a shape that corresponds to the shape of the surface of the specimen 30 that it will make contact with when the applicator 150 is applying a load. In the exemplary embodiment shown by FIG. 2, the face 165 has a shape that permits the face 165 to accommodate a specimen having a roughly flat surface, for example, a plank, and is recessed to ensure that the specimen 30 remains stable on the face 165 during loading. In one embodiment, the face 165 has a roughly rectangular surface area, but any suitable shape for making contact with a surface of a specimen 30 and applying a load from the load applicator 150 for testing purposes is possible in other embodiments. Additionally, other surface profiles and configurations of the face 165 are possible in other embodiments.

In this regard, the specimen 30 passes over the face 165 when the specimen 30 is placed in the system 10 such that the face 165 contacts the specimen 30 such that the load applicator 150 applies a load to the specimen 30 (i.e., it presses the specimen 30) at the point where the specimen 30 makes contact with the face 165. Thus, the face 165 can direct a load applied by the load applicator 150 to the specimen 30.

Note that, in the exemplary embodiment shown by FIG. 1, the interface 155 is oriented such that the holes 160 are aligned along the longitudinal axis of the specimen 30. In this regard, the interface 155 is configured for applying a load from the load applicator 150 to the specimen 30 while the specimen is inserted through the bearing 55 and inserted into the chuck 54.

In an exemplary embodiment, the interface 155 is rotatable. Depending on the type of loading desired and the type of specimen 30 to be tested, a user may rotate the interface 155 in order to properly align the interface with the specimen 30 as the user places it into the system 10 for testing. For example, when rotation of a specimen 30 is desired after a load is applied to the specimen 30, the user may rotate the interface 155 until the holes 160 are properly aligned with the respective holders 25, in this case, the bearing 55 and chuck 54. Then, a specimen 30 may be passed through the bearing 55 and holes 160 (i.e., from the X-axis direction) and coupled to the chuck 54, such as is described above and depicted by FIG. 1. Note that, in some embodiments, such that the holes 160 and face 165 may be aligned to interact with a specimen 30 that is in a variety of orientations so that a load may be applied from the load applicator 150. Alternatively, as shown by FIG. 2, if a user desires to apply a load to a specimen 30 without rotating the specimen 30, the user may rotate the interface 155 until the face 165 is properly aligned with the respective holders 25, here the slot 65 and stop 64 (i.e., the specimen 30 passes through the slot 65 and fits under the stop 64). In one embodiment, the interface 155 may be rotated ninety (90) degrees about the Y-axis, such that a user may align the holes 160 or the face 165 with a surface of the specimen 30 to be tested (i.e., the specimen 30 passes through the holes 160 or sits in the face 165, as desired), but the interface 155 may rotate any number of degrees about any of the X, Y, or Z axes in other embodiments. Note that it is not necessary for the interface 155 to be rotatable. It is also unnecessary for the interface 155 to have either holes 160 or a face 165, and the interface 155 may apply a load from the load applicator 150 to a specimen 30 via other means suitable for applying a load from the load applicator 150 to a specimen 30 in other embodiments.

An exemplary embodiment of the specimen rotation system 250 is shown by FIG. 1. After applying a load to a specimen 30, a user may desire to rotate the specimen 30 while applying the load in order to induce rotational bending fatigue. In this regard, the force experienced by a given portion of the specimen 30 oscillates between periods of compression and tension as the specimen 30 rotates. During rotation, the user may to adjust the load via adjustment to the load applicator 150, as described above, or may leave the load 150 constant while the specimen 30 is rotating. The user may continue to rotate the specimen 30 until the desired number of rotations is reached or until the specimen 30 fails. Note that, in the embodiment of FIG. 1, the specimen rotation system 250 is responsive to user input and rotates a specimen 30 gripped by the chuck 54 about the longitudinal axis of the specimen 30 (i.e., about the X-axis direction). The specimen rotation system 250 shown by FIG. 1 uses a hand crank, shafts and a gear train to rotate the specimen 30, but the system 250 may comprise any suitable device or system for transmitting the desired rotation to the specimen 30 in other embodiments.

The system 250 has a hand crank 260 with a handle 265 that enables a user to rotate the hand crank 260 efficiently. The hand crank 260 is supported by a crank support 268 that is roughly rectangular in shape, couples to the base member 33 and oriented roughly parallel to the supports 31 and 32. The hand crank 260 is coupled to a crankshaft 270 that passes through the crank support 268 and right support 32. The crankshaft 270 rotates with the hand crank 260 as the user provides rotation. The crankshaft 270 is coupled to a large gear 275 adjacent to the right support 32 that transmits the rotation of the crankshaft 270 by interacting with a small gear 280. The small gear 280 is adjacent to the right support 32 and is coupled to a spindle 285 that passes through the crank support 268 and right support 32 before it couples to the chuck 54. In this regard, as a user rotates the hand crank 260, the rotation is transmitted to the spindle 285, which rotates the chuck 54 to which a specimen 30 is coupled. In other embodiments, other devices to apply the desired rotation to a specimen 30 are possible.

Note that, in one embodiment, the crankshaft 270 and spindle 285 pass through bearings (not specifically shown) in the crank support 268 and right support 32, respectively. In this regard, the bearings (not specifically shown) permit the crankshaft 270 and spindle 285 to rotate about the X-axis as the user provides rotation using the hand crank 260.

The exemplary embodiment of the system 10 shown by FIG. 1 has a sensor 300 for measuring force applied by the load applicator 150. In one embodiment, the sensor 300 is implemented as a pressure sensor. The sensor 300 is situated between the base member 33 and the load applicator 150. When the load applicator 150 applies a load to a specimen 30, the sensor 300 is compressed between the applicator 150, and the base member 33. In this regard, the sensor 300 should experience and measure an amount of compressive force that is equal to the load (i.e., amount of force) that the applicator 150 is applying to the specimen 30 in the Y-axis direction.

In an exemplary embodiment, the sensor 300 is coupled to a force display 310 that is readable by a user of the system 10. The display 310 provides a visual representation (i.e., a reading) of the amount of force that is measured by the sensor 300 at a given time. The display 310 depicted by FIG. 1 is implemented as a conventional analog dial with a readout, but other devices capable of displaying a visual representation of the amount of force experienced by the sensor 300 are possible in other embodiments. In yet other embodiments, the display 310 may display a force reading from the sensor 300 electronically, for example, on an output device, such as a monitor or a screen. Note that it is not necessary to have a display 310 in all embodiments.

The exemplary embodiment of FIG. 1 further depicts a deflection sensor 314 coupled to the interface 155 for reading amount of deflection that a specimen 30 is experiencing at a given time. In the instant embodiment, the sensor 314 is implemented as a conventional mechanical deflection sensor (e.g., using springs to measure deflection), but other deflection sensors, such as electrical sensors comprising transducers or linear variable differential transformers (LVDTs), are possible in other embodiments. The sensor 314 is coupled to the interface 155 such that there is sufficient space between the face 165 and the sensor 314 for a specimen 30 to pass through. For example, the sensor 314 senses the amount of deflection that a specimen 30 is experiencing when the load applicator 150 applies a sufficient load to the specimen 30 to cause the specimen 30 to undergo deflection that can be sensed by the sensor 314. In one embodiment, the sensor 314 senses the deflection of the specimen 30 when the specimen 30 makes contact with and applies pressure to a surface of the sensor 314. In this regard, the sensor 314 measures an amount deflection. Note that the sensor 314 may be situated in other locations of the system 10 suitable for measuring deflection of a specimen 30 in other embodiments.

Additionally, the exemplary sensor 314 of FIG. 1 has deflection display 315 that is readable by a user of the system 10. The display 315 provides a visual representation the amount of deflection that is measured by the sensor 314 at a given time. The display 315 depicted by FIG. 1 is implemented as a conventional analog dial with a readout, but other devices capable of displaying a visual representation of the amount of deflection experienced by the specimen 30 are possible in other embodiments. In yet other embodiments, the display 315 may display a deflection reading from the sensor 314 electronically, for example, on an output device, such as a monitor or screen. Note that it is not necessary to have a display 315 in all embodiments, for example when the beam 35 comprises a ruler or other device for measuring and determining deflection of a specimen 30.

In an exemplary embodiment, system 10 further comprises a counter 325 for counting the number of rotations applied to a specimen 30 by the specimen rotation system 250. The counter 325 is coupled to a counter pulley 330 that shares a common pulley belt 335 with crankshaft pulley 340 that is coupled to the crankshaft 270. In this regard, the crankshaft pulley 340 rotates concurrently with the crankshaft 270, and the counter pulley 330 rotates concurrently with the crankshaft pulley 340 by virtue of sharing the pulley belt 335. Thus, the counter pulley 330 experiences essentially the same rotation as the crankshaft 270 driven by user input using the hand crank 260.

In the instant embodiment, the counter 325 is implemented as a mechanical rotary counter that counts up by one for each full rotation (i.e., 360 degrees) of the counter pulley 330. As noted above, the crankshaft 270 is coupled to the chuck 54, which is coupled to the specimen 30. For each full rotation of the crankshaft 270, the crankshaft pulley 340 rotates the counter pulley 330 by a full rotation via the pulley belt 335. The counter 325 counts up by one count whenever it senses that the counter pulley 330 has completed a full rotation. In this regard, the counter 325 counts the number of rotations of the specimen 30 applied by the user via the specimen rotation system 250. Furthermore, the exemplary counter 325 of FIG. 1 comprises an output device (not specifically shown) that provides feedback to the user that is indicative of the number of rotations of the counter pulley 330 that the counter 325 has counted. The output device (not specifically shown) may comprise a monitor, a display, or other device for providing feedback indicative of the number of rotations of the specimen 30. Note that the counter 325 may comprise output devices (not specifically shown) in other embodiments. Note also that a user may reset the counter to zero and begin counting again when desired.

Figure 3:
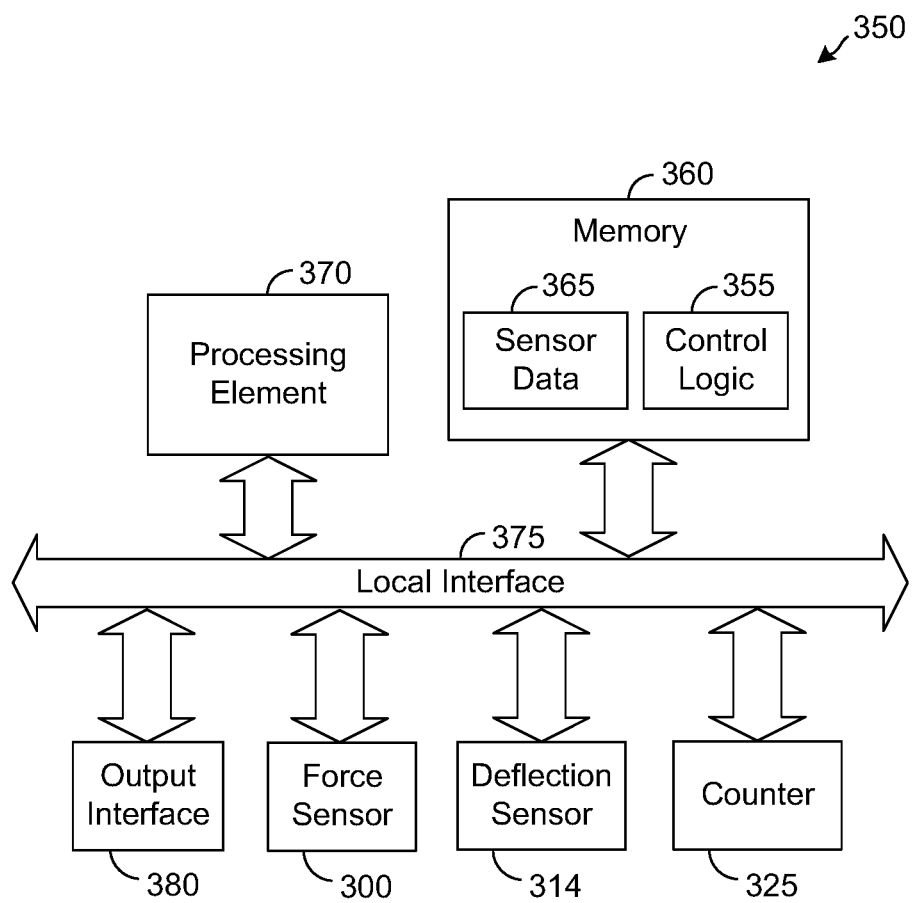
FIG. 3 is a block diagram illustrating an exemplary embodiment of a controller.

FIG. 3 depicts an exemplary embodiment of a controller 350. The controller 350 includes control logic 355 for generally controlling the operation of the controller 350. The control logic 355 can be implemented in software, hardware, firmware, or any combination thereof. In the exemplary controller 350 illustrated by FIG. 3, the control logic 355 is implemented in software and stored in memory 360 of the controller 350. Note that the control logic 355, when implemented in software, can be stored and transported on any computer-readable medium for use by or in connection with an instruction execution apparatus that can fetch and execute instructions.

The controller 350 further comprises sensor data 365 that includes information (i.e. measurements) received from sensors of the system 10 (e.g., sensor 300 and sensor 314) to which the controller 350 is coupled. The sensor data 365 includes data from the sensor 300 that is indicative of the amount of force applied by the load applicator 150 to the specimen 30, data from the sensor 314 that is indicative of the deflection of the specimen 30, and data from the counter 325 that is indicative of the number of rotations experienced by the specimen 30. The sensor data 365 can include other data from other sources in other embodiments. In one embodiment, the controller 350 is coupled communicatively to the sensor 300 and the sensor 314, for example, via conductive means or via short-range communication protocol, such as Bluetooth®.

The exemplary controller 350 depicted by FIG. 3 includes at least one conventional processing element 370, which includes processing hardware for executing instructions stored in memory 360. As an example, the processing element 370 may include a central processing unit (CPU) or a digital signal processor (DSP). The processing element 370 communicates to and drives the other elements within the controller 350 via a local interface 375, which can include at least one bus. In addition, the controller 350 has an output interface 380, for example a display screen, which can be used to output data to the user of the system 10.

In an exemplary embodiment, the user places a specimen 30 into the system 10 and conducts the desired testing (i.e., applies the desired load and/or rotation to the specimen 30, as described above). The sensors 300 and 314 and counter 325 record their respective data, as described above. The control logic 355 reads the sensors 300 and 314 and counter 325 and retrieves data that is indicative of the load applied to the specimen 30 by the load applicator 150, the deflection of the specimen 30, and the number of rotations applied to the specimen 30 during testing. The control logic 355 stores the data read from each of the sensors 300 and 314 and counter 325 in memory 360 as sensor data 365. The control logic 355 can extract the data stored as sensor data 365 and output it to a user of the system 10 via the output interface 380. In this regard, the controller 350 is configured to provide data that is indicative of the results of testing performed on a given specimen 30 based on the sensor data 365 to a user of the system 10 as desired (e.g., in "real time").

In an alternative embodiment, the controller 350 also controls the functions of the load applicator 150 and specimen rotation system 250 based on input from a user. A driver (not shown), such as a motor, generator, or other device capable of providing mechanical energy, provides output to the load applicator 150 and the specimen rotation system 250 to apply the desired load and rotation to a specimen 30. Note that the controller 350 is coupled communicatively to a communication interface (not shown) of the driver (not shown). In some embodiments, the controller 350 may be communicatively coupled to the driver (not shown) conductively or via short-range communication protocol, such as Bluetooth®. In this regard, the control logic 355 can control the functions of (i.e., adjust) each of the load applicator 150 and specimen 250 by controlling the output of the driver (not shown) based on input from a user the controller 350 receives via an input interface (not shown). Additionally, the user may view data that is indicative of the output of the driver (not shown) and data that is stored as sensor data 365 as described above via the output interface 380.

The exemplary system 10 of FIG. 1 is completely mechanically powered, though the various components of the system 10 may be implemented as devices powered by various means (e.g., electrically, pneumatically, hydraulically, or otherwise). In the instant embodiment, the system 10 is implemented as a man-portable device, weighing twenty (20) pounds or less and having a plurality of carry handles 400. The two carry handles 400 depicted by FIG. 1 are coupled to the left support 31 and crank support 268 and permit a user to transport the system 10 by hand. In other embodiments, additional configurations and locations of the plurality of handles 400 are possible.

Now, therefore, the following is claimed:

1. A specimen testing system, comprising:
a frame having a plurality of specimen holders, including at least a first specimen holder and a second specimen holder;
a specimen coupled to the first specimen holder; and
a load applicator configured to apply a load to the specimen between points where the specimen contacts the plurality of specimen holders, wherein the load applicator has an interface contacting a surface of the specimen, wherein the interface is rotatable between a first position and a second position, wherein the interface has a plurality of holes for receiving the specimen when the interface is in the first position, and wherein the interface has a face for contacting and supporting the specimen when the interface is in the second position.

2. The specimen testing system of claim 1, wherein the first specimen holder comprises a clamp.

3. The specimen testing system of claim 1, wherein the first specimen holder comprises a chuck.

4. The specimen testing system of claim 1, wherein the frame further comprises a first support having a slot, wherein the specimen passes through the slot.

5. The specimen testing system of claim 1, wherein the frame further comprises a first support having a bearing, wherein the specimen passes through the bearing.

6. The specimen testing system of claim 1, further comprising a specimen rotation system coupled to the first specimen holder, wherein the first specimen holder is rotatable about a longitudinal axis of the specimen and wherein the specimen rotation system is responsive to user input for rotating the first specimen holder.

7. The specimen testing system of claim 1, wherein the load applicator comprises a jack.

8. The specimen testing system of claim 7, wherein the load applicator is configured to apply the load in a direction that is perpendicular to a longitudinal axis of the specimen.

9. The specimen testing system of claim 1, wherein the interface further comprises one or more tabs adjacent to the face for contacting and stabilizing the specimen when the interface is in the second position.

10. The specimen testing system of claim 1, wherein the interface has two parallel sides separated by a hollow region, the sides each having a hole of the plurality of holes for receiving the specimen.

11. The specimen testing system of claim 1, wherein the load applicator is configured to apply the load to the specimen at points where the specimen contacts the interface.

12. The specimen testing system of claim 1, wherein the interface has a face parallel to a surface of the specimen for applying the load from the load applicator.

13. The specimen testing system of claim 1, further comprising a controller for controlling sensors, wherein the sensors measure data indicative of the load applied to the specimen.

14. The specimen testing system of claim 1, wherein the interface comprises a deflection sensor.

15. The specimen testing system of claim 14, wherein the specimen passes between a portion of the deflection sensor and the face.

16. The specimen testing system of claim 14, wherein the deflection sensor comprises a linear variable differential transformer.

17. A method of testing specimens, comprising:
providing a specimen testing system having a frame and a load applicator, wherein the load applicator comprises an interface having a plurality of holes, the interface rotatable between a first position and a second position;
coupling a first specimen to a first specimen holder of the frame and a second specimen holder of the frame;
inserting the first specimen through the plurality of holes while the first specimen is in the first position;
applying a first load from the load applicator to the first specimen between points where the specimen contacts the first specimen holder and the second specimen holder while the first specimen is passing through the plurality of holes;
rotating the first specimen holder to which the specimen is coupled while applying the load to the specimen from the load applicator;
rotating the interface to the second position;
coupling a second specimen to the first specimen holder and the second specimen holder;
contacting the second specimen with a face of the interface while the interface is in the second position; and
applying a second load from the load applicator to the second specimen between points where the specimen contacts the first specimen holder and the second specimen holder while the second specimen is contacting the face.

18. A specimen testing system, comprising:
a frame having a plurality of specimen holders, including at least a first specimen holder and a second specimen holder;
a load applicator configured to apply a load to a specimen held by the first specimen holder and the second specimen holder, wherein the load applicator has an interface for contacting a surface of the specimen, wherein the interface is rotatable between a first position and a second position, wherein the interface has a plurality of holes for receiving the specimen when the interface is in the first position, and wherein the interface has a face for contacting and supporting the specimen when the interface is in the second position; and
one or more sensors for sensing the load applied by the load applicator, wherein at least one of the one or more the sensors is configured to provide an output indicative of the sensed load.

* * * * *